United States Patent [19]

Ellis, Jr. et al.

[11] Patent Number: 4,895,680
[45] Date of Patent: Jan. 23, 1990

[54] HYDROCARBON OXIDATIONS CATALYZED BY NITRIDE-ACTIVATED METAL COORDINATION COMPLEXES

[75] Inventors: Paul E. Ellis, Jr., Downingtown; James E. Lyons, Wallingford; Harry K. Myers, Jr., Cochranville, all of Pa.

[73] Assignee: Sun Refining and Marketing Company, Philadelphia, Pa.

[21] Appl. No.: 247

[22] Filed: Jan. 2, 1987

[51] Int. Cl.$^4$ .................. C07C 67/00; C07C 27/12; C07C 45/32; C07C 45/33

[52] U.S. Cl. .................. 260/410.9 R; 260/413; 560/241; 560/241.1; 562/512.2; 562/549; 568/398.8; 568/399; 568/910; 568/910.5

[58] Field of Search .................. 562/549, 512.2; 568/398.8, 399, 910, 910.5; 560/241, 241.1; 260/440.9 R, 413

[56] References Cited

U.S. PATENT DOCUMENTS

| | | | |
|---|---|---|---|
| 3,816,548 | 6/1974 | Williams et al. | 568/399 X |
| 3,873,625 | 3/1975 | Barone | 568/399 X |
| 4,028,423 | 6/1977 | Brownstein et al. | 568/399 X |
| 4,459,427 | 7/1984 | Middleton et al. | 568/910 X |

OTHER PUBLICATIONS

J. E. Lyons, Hydrocarbon Processing, Nov. 1980, p. 107, Table I.

Taylor et al., J. Chem. Soc. Chem. Comm. 279 (1984).
Mansuy et al., ibid., 253 (1983).
Groves et al., J. Am. Chem. Soc., 102, 6377 (1980).
Hill et al., ibid., 102, 6374, (1980).
Smegal et al., ibid., 105, 5515, (1983).
Tabushi et al., ibid., 103, 7371, (1981).

Primary Examiner—Werren B. Lone
Attorney, Agent, or Firm—J. Edward Hess; Donald R. Johnson

[57] ABSTRACT

Hydrocarbon, and particularly lower molecular weight alkanes and cycloalkanes, may readily be oxidized with air or $O_2$ to form such products as alcohols, ketones, and the like in high yields when there is employed as the catalyst a highly active nitride-activated metal coordination complex having the structure

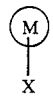

where M is a transition metal; " ◯ " is a ligand; and X is a nitride. Certain dimeric forms of the above catalyst are also employed herein. It has also been discovered that Group IV through VIII transition metal nitrides are also highly effective oxidation catalysts for lower molecular weight hydrocarbons such as alkanes.

20 Claims, No Drawings

HYDROCARBON OXIDATIONS CATALYZED BY NITRIDE-ACTIVATED METAL COORDINATION COMPLEXES

BACKGROUND OF THE INVENTION

1. Field of the Invention

This invention relates to a novel process for the oxidation of hydrocarbons. More particularly, this invention relates to the catalytic oxidation of a wide range of oxidizable hydrocarbons, particularly alkanes, with air or oxygen. The catalyst is a ligand complex of transition metals activated by a nitride group bonded to the metal.

2. Background of the Invention

The oxidation of alkanes and other aliphatic hydrocarbons catalyzed by transition metal complexes in the liquid phase is well known in the art, and commercial applications of this technology are extensive. See, for example, J. E. Lyons, Hydrocarbon Processing, Nov., 1980, page 107, Table I.

However, the oxidation of unactivated hydrocarbons such as methane, ethane, propane, butanes and the like by air or $O_2$ as the oxidant is extremely difficult to achieve. The use of macrocyclic metal complexes such as metalloporphyrins as catalysts in the liquid phase has not been successful in giving rapid rates and high selectivities under mild conditions using air or $O_2$ as the oxidant. Some success has been achieved using two less economically desirable approaches:

(1) The use of metalloporphyrin catalysts such as Fe(TPP)Cl and Mn(TPP)Cl (where TPP=the dianion of 5, 10, 15, 20-tetraphenylporphine) with iodosylbenzene, sodium hypochlorite, alkylhydroperoxides or other expensive, non-regenerable oxidants. [P. Traylor, D. Dolphin, and T. Traylor, *J. Chem. Soc. Chem. Comm.*, 279 (1984); J. Groves, W. Kruper, Jr., R. Haushalter, *J. Am. Chem. Soc.*, 102, 6377 (1980) ; C. Hill, B. Schardt, *J. Am. Chem. Soc.*, 102, 6374 (1980); J. Smegal and C. Hill, *J. Am. Chem. Soc.*, 105, 3515 (1983); A. Middleton and D. Smith, U.S. Pat. No. 4,459,427 (Jul. 10, 1984)]; or (2) The use of metalloporphyrin catalysts with molecular oxygen as oxidant and simultaneous addition of a reductant such as $NaBH_4$, ascorbic acid or colloidal platinum with $H_2$. Again, the added reagents are expensive and non-regenerable. Examples of this approach can be found in D. Mansuy, M. Fontecave and J. Bartoli, *J. Chem. Soc. Chem., Comm.* 253 (1983); I. Tabushi and A Yazaki, *J. Am. Chem. Soc.*, 103, 7371 (1981).

It is, therefore, an object of this invention to provide a nitride-activated metal coordination complex-catalyzed process for the oxidation of hydrocarbons, and particularly alkanes, using air or oxygen, but without the need for added expensive, non-regenerable oxidants, reductants, or other co-catalysts.

SUMMARY OF THE INVENTION

In accordance with the present invention, it has now been found that hydrocarbons generally, and alkanes in particular, desirably those hydrocarbons having from about 1 to 20 carbon atoms, and preferably those having from 1 to 10 carbon atoms, may readily be oxidized with air or oxygen to selectively form the corresponding hydrocarbon oxidation products such as acids, alcohols, ketones, esters, and the like, or mixtures thereof, when the catalyst is certain nitride-activated metal coordination complexes, as defined below. More particularly, it has been found that coordinating a nitride ion to certain metal coordination complexes can convert a complex which is otherwise catalytically inactive, or has low catalytic activity, into a highly active catalyst for the selective oxidation of difficult-to-oxidize alkanes to form alcohols, ketones, or mixtures thereof, in good yield with little burn to carbon oxides.

By virtue of the use of these catalysts in the oxidation of hydrocarbons, and especially alkanes, many surprising and unexpected advantages accrue. For example, the reaction can be carried out at lower temperatures than heretofore employed; there is often little or no cleavage of the starting material; there is little or no burn to form CO or $CO_2$; there is higher selectivity for alcohols, when alcohols are the desired product; the reaction rates are generally faster than those of comparable prior art processes; and the processes themselves are less expensive than those of the prior art which require strong oxidants. In some instances, such as the oxidation of ethane, propane, and the like, selective oxidations can be performed which have not been achieved to date, using the coordination complexes of this invention.

DESCRIPTION OF THE INVENTION

The process of this invention, which is applicable to hydrocarbons of virtually unlimited carbon atom content, is uniquely applicable to alkanes, which are known to be more difficult to oxidize than other types of hydrocarbons. However, it will be understood that the aforesaid catalysts are equally effective in the oxidation of other classes of hydrocarbons as well, especially those containing substituents which will enhance the reactivity of the carbon-hydrogen bond with oxygen, i.e. "activated hydrocarbons", as described below.

As aforestated, this process is particularly effective in the oxidation of alkanes, including cycloalkanes, substituted alkanes and the like. The alkane starting materials thus include straight and branch-chain compounds having from about 1 to 20 carbon atoms, preferably 1 to 10 carbon atoms such as methane, ethane, propane, n-butane, isobutane, n-pentane, n-hexane, 3-methylpentane, 2-methylpentane, heptane, 2-methylheptane, 3-methylheptane and the like, as well as cycloalkanes having from about 5 to 20 carbon atoms, preferably 5 to 10 carbon atoms, such as cyclohexane, cyclopentane, cycloheptane, cyclooctane, and the like. These compounds, if desired, may be substituted with various moieties, although care should be taken to exclude substituents which will adversely affect the activity of the catalyst.

When the foregoing alkanes are oxidized in accordance with the process of this invention, the corresponding alcohols, ketones, and the like are obtained. Thus, this process is generally applicable to the preparation of a broad class of known materials which may be used, for example, as solvents, chemical intermediates, commodity chemicals, polymer intermediates, gasoline additives, and the like.

Illustrations of activated hydrocarbons which may also be oxidized by the process of this invention include such compounds as toluene, xylenes, cumene, ethylbenzene, diphenylmethane, fluorene, and like alkyl-substituted aromatics having from about 7 to 20 carbon atoms, preferably 7 to 12 carbon atoms. Also included are olefinic hydrocarbons, particularly those containing allylic bonds, as for example, propylene, butenes, cyclohexene, and the like. In addition, it should be understood that the catalysts of this process are able to oxidize olefinic double bonds directly in many instances to give epoxides, ketones and alcohols, which are also useful as solvents, chemical intermediates, and the like. The olefins desirably have from about 2 to 20 carbon atoms, preferably 2 to 8 carbon atoms.

Finally, the process of this invention is also applicable to the further oxidation of partially oxidized hydrocarbons other than, of course, organic acids. Thus, for example, partially oxidized hydrocarbons such as alcohols and aldehydes may be oxidized to a more highly oxidized state, using the catalysts of this invention. Generally these partially oxidized hydrocarbons have from about 1 to 20 carbon atoms, that is, they are the same hydrocarbons as described about except for being partially oxidized.

Thus, from the foregoing description of the starting materials, it will be seen that this process is widely applicable to a broad range of oxidizable hydrocarbons, of which the oxidation of alkanes represents a preferred embodiment of this invention. As stated above, these hydrocarbons may contain various substituents on them as long as they do not adversely affect the activity of the catalyst.

The oxidation, which may be carried out in a generally known manner, is desirably conducted in the liquid phase, using such organic solvents as benzene, acetic acid, acetonitrile, methyl acetate, or like solvents which are inert to the conditions of the reactions, or in a neat solution of the hydrocarbon if it is liquid and pressures ranging from about 15 to 1500 psig, preferably 30 to 750 psig, at temperatures of from about 25° to 250° C., more preferably 70° to 180° C. Depending upon whether the hydrocarbon to be oxidized is a solid, liquid, or gas, it is dissolved in or bubbled through the solvent, together with air or oxygen, in the presence of the aforementioned nitride-activated metal coordination complex catalyst for periods of time sufficient to yield the desired oxidized product, generally from about 0.5 to 100 hours, and more preferably from 1 to 10 hours.

The nature of the solvent, while not critical, can have an effect on the rates and selectivities obtained and should be selected carefully in order to optimize the desired results. For example, it has been found that solvents such as acetonitrile and acetic acid are often very effective for the oxidation of alkanes to form oxygen-containing compounds, whereas reactions carried out in such solvents as methyl acetate or benzene may occur more slowly. Thus, by routine experimentation the optimum solvent for the particular process can readily be determined.

The ratios of the various reactants may vary widely, and are not critical. For example, the amount of catalyst employed can range from about $10^{-6}$ to $10^{-3}$ moles per mole of hydrocarbon such as alkane, and more preferably from about $10^{-5}$ to $10^{-4}$ moles of catalyst per mole of hydrocarbon, although other amounts are not precluded; while the amount of oxygen relative to the hydrocarbon starting material may vary widely, generally $10^{-2}$ to $10^{-2}$ moles of oxygen per mole of hydrocarbon. Care should be taken since some of these ratios fall within explosive limits. As a group, the catalysts are almost always soluble unless used in large excess. Thus, as a rule the reactions are generally carried out as solution phase reactions.

Many of the catalysts employed in this process are generally known compounds, or else may readily be prepared in accordance with established methods. These catalysts, as mentioned above, may best be defined as nitride-activated metal coordination complexes having the following general structure:

wherein M is a metal in the transition series from Groups IV(a) to VIII, such as Ti, V, Cr, Mn, Fe, Co, Nb, Mo, Ru, Rh, W, Os, Ir, or the like; X is nitride ($N^{3-}$); the component depicted as " " comprises a ligand such as tetraphenylporphyrin, related porphyrinate ligands, porphycenes, porphenes, phthalocyanines, 1,3-bis (2-pyridylimino) isoindoline ("BPI"), and other 1,3-bis (arylimino) isoindolines, acetylacetonates, acetates, hydroxides, or a Schiff base such as salen, saleph, or the like. Thus, by the term "ligand", as used herein, is meant any group or system of atoms coordinated to a transition metal center which forms one or more bonds to the metal, as defined above, i.e. forms a coordination complex, and stabilizes this transition metal coordination complex in desirable oxidation states. Preferred amongst these ligands are such macrocyclic groups as porphyrins, phthalocyanines, 1,3-bis (arylimino) isoindolines, Schiff bases, and the like. Examples of ligands which may be employed in the catalysts of this invention are such mono-, bi-, tri-, and tetradentate ligand systems as: hydroxides, acetates, propanoates, butyrates, benzoates, naphthenates, stearates, acetylacetonates, and other β-diketones, 1,3-bis (arylimino) isoindolinates, salen, saleph, porphyrinates, porphycenates, porphenates, phthalocyanates, and like systems.

In addition to the foregoing ligands there may also be employed in the catalysts of this invention such other ligands as bipyridines, terpyridines, phenanthrolines, dithiocarbamates, xanthates, salicylaldimines, cyclam, dioxocyclam, pyrazoylborates, and tetraazamacrocycles such as tetramethyltetraazadihenzocyclotetradecane.

It is known in the art to halogenate ligands such as those described above in order to increase the oxidation resistance thereof, which thereby improves catalyst life. Usually the halogen is chlorine or fluorine as in tetrachlorotetraphenylporphorinato. As used herein, the term ligand includes the halogenated type also.

It has also been found that a modified form of the above-described nitride-activated metal coordination complex, i.e. a dimer of said complex as defined below, is likewise an effective oxidation catalyst for hydrocarbons, especially alkanes and cycloalkanes. These dimers, which are closely related to the above catalysts, have the structural formula:

wherein M, X, and " " are as defined above, i.e. M is a transition metal, X is nitride, and " " is a ligand.

The catalysts described and employed herein are either known or can readily be prepared by procedures described in the art, starting with known metal coordination complexes and/or literature preparations for making such complexes. In most cases, the preparation of the metal nitride catalysts of this invention involves either photolysis or thermolysis of the corresponding transition metal azide complexes, or high temperature reactions of metal ligand complexes with sodium azide which forms the nitride in one step. The transition metal azide complexes which may be employed in the preparation of these nitride catalysts may themselves be prepared in accordance with the teachings in copending application, Ser. No. 246, filed Jan. 2, 1987 in the names of Ellis et al, the teachings of which application are incorporated herein by reference. In general, the transition metal azide complexes, many of which are described in the literature, are prepared by reactions between known metal coordination complexes having a metal halide, acetate, hydroxide, or similar group, and either hydrazoic acid or sodium azide.

Illustrations of the preparation of the certain of the nitride-activated metal coordination complexes of this invention are as follows:

Mn(TPP)N or Cr(TPP)N can be synthesized by the photodissociation of their corresponding azide complexes in benzene or THF solvent. (See J. W. Buchler et al, *Z. Naturforsch.*, 39b 222–230 (1984).

Mn(TPP)N and Cr(TPP)N can also be prepared by the action of ammonia and hypochlorite ion on Mn(TPP)OH and Cr(TPP)OH respectively. (See J. W. Buchler et al, *Inorg. Chem.*, 22, 879–884 (1985). Nearly all nitride complexes are prepared by either the decomposition of azido complexes or the reduction of ammonia complexes.

Alternatively, the dimer [Fe(TPP)]$_2$N, for example, can be prepared by the thermal decomposition of Fe(TPP)N$_3$ in xylene. (See D. A. Summerville et al, *JACS*, 98, 1747–52 (1976).) Also, the dimer [Fe(Pc)]$_2$N can be prepared by the reaction of Fe(Pc) with NaN$_3$ in refluxing chloronaphthalene. (See L. A. Bottomley et al, *Inorg. Chem.*, 24, 3733–37 (1985).)

In a like manner those skilled in the art can readily prepare other nitride catalysts by the general procedures and literature teachings described above, employing the corresponding ligated azides described in the above-mentioned copending application Ser. No. 246 as the starting material.

From the foregoing it will be seen that the catalysts of this invention are comprised of three component parts: the ligand moiety, the transition metal which is bound to (i.e., complexed with) the ligand, and the nitride group, which is bound to the transition metal.

The nature of the X group, namely nitride, which comprises the third component of the catalysts of this invention significantly affects the activity of the final catalyst. Surprisingly, other known groups such as chloride, acetate, benzoate and the like provide very poor if any results and should be avoided in the oxidation of most alkanes. While applicants do not wish to be bound by any particular theories, it is believed that the reason that the nitride group is effective for purposes of activating the metal complexes of this invention is due to its electron-donating properties with respect to the transition metal component.

While the effectiveness of a particular catalyst may depend in part on the nature of the hydrocarbon starting material, selection of the catalyst for oxidizing any particular hydrocarbon can be readily determined by those skilled in the art. Examples of those catalysts which are most preferred, particularly for oxidation of lower alkanes, include such compounds as tetraphenylporphyrinato manganese (V) nitride, tetraphenylporphyrinato chromium (V) nitride, ($\mu$-nitrido) bis (phthalocyaninato) iron (III$\frac{1}{2}$), and the like.

The process of this invention will now be illustrated by, but is not intended to be limited to, the following examples.

EXAMPLES

A series of runs were carried out employing a variety of catalysts, alkanes, solvents, and operating conditions, as shown in Tables I to III below, together with the resulting products.

Except where shown otherwise in the tables, these runs were carried out as follows: the alkane was dissolved in an appropriate solvent containing the catalyst, and oxygen was added to the desired pressure. Oxidation was carried out at the designated temperature for the time listed in the tables. Gases and liquid products were analyzed by GC and MS.

In the following examples, activity is measured in terms of "turn over number" (T.O.N.) i.e. moles of product/mole of catalyst, unless otherwise designated in the tables, (acac) is acetylacetonate, TPP is tetraphenyl-porphorinato, Pc is phthalocyaninato, IPA is isopropylacohol, amounts of products are mmoles/gram of reaction mixture, except in Table III where it is millimoles absolute.

Examples 1–5

Propane was oxidized in a small, glass-lined rocking autoclave under the conditions indicated in Table I. Tetraphenylporphorinatomanganese (V) nitride was compared with a typical autoxidation catalyst: Co(acac)$_3$.

TABLE I

| | EFFECTS OF NITRIDE ON METAL CATALYZED OXIDATION OF PROPANE[a] | | | | |
|---|---|---|---|---|---|
| | | REACTION | PRODUCTS | | |
| EXAMPLE | CATALYST - moles/l | TIME/HRS. | ACETONE | IPA | T.O.N |
| 1 | Co(acac)$_3$ 0.032 | 5.0 | 0.14 | 0.19 | 57 |
| 2 | Co(acac)$_3$ 0.032 | 12.8 | 0.26 | 0.15 | 89 |
| 3 | Co(acac)$_3$ 0.032 | 60.5 | 0.23 | 0.17 | 87 |
| 4 | Mn(TPP)N 0.006 | 13.0 | 0.18 | 0.18 | 383 |
| 5 | Mn(TPP)N 0.006 | 61.8 | 0.41 | 0.30 | 828 |

[a]Catalyst was dissolved in 7 ml benzene. Propane was oxidized by air at about 1200 psig total pressure at 150° C.

Examples 6–12

Propane was oxidized in a 300 ml glass-lined stirred autoclave as indicated in Table II. Tetraphenylporphyrinatomanganese (V) nitride, tetraphenylporphyrinato chromium (V) nitride, and bisphthalocyaninatoiron(III½) nitride were compared with a typical autoxidation catalyst, i.e. Co(acac)₃.

these catalysts are effective at temperatures of from about 75° to 250° C., preferably 100° to 200° C., with

TABLE II

PROPANE OXIDATION IN 300 Ml. STIRRED AUTOCLAVE[a]

| EXAMPLE | CATALYST | CATALYST (mM.) | BENZENE (g.) | PROPANE (mM.) | TIME (HOURS) | PRODUCTS ACETONE | IPA | T.O.N. | T.O.N./ HOUR |
|---|---|---|---|---|---|---|---|---|---|
| 6 | Co(acac)₃ | 0.320 | 70.32 | 568 | 2.0 | 0.190 | 0.009 | 6.3 | 3.1 |
| 7 | Co(acac)₃ | 0.320 | 70.32 | 568 | 8.1 | 0.024 | 0.0 | 5.3 | 0.7 |
| 8 | Mn(TPP)N | 0.060 | 70.32 | 568 | 8.0 | 0.118 | 0.010 | 156.7 | 19.6 |
| 9 | [Fe(Pc)]₂N | 0.036 | 42.20 | 682 | 7.2 | 0.214 | 0.029 | 282.9 | 39.1 |
| 10 | Cr(TPP)N | 0.036 | 42.20 | 682 | 4.0 | 0.049 | 1.771 | 79.2 | 19.8 |
| 11 | Cr(TPP)N | 0.036 | 42.20 | 682 | 8.0 | 0.079 | 1.937 | 115.3 | 14.4 |
| 12 | Cr(TPP)N (200° C.) | 0.036 | 42.20 | 682 | 8.0 | 0.28 | 0.097 | 457.6 | 57.2 |

[a]Reactions were performed at 150° C., unless noted. The propane was oxidized by air at about 1000 psig. The solvent was benzene.

Examples 13–18

Cyclohexane was oxidized in a 300 ml autoclave with an oxygen-containing gas constantly sparging through the system under the conditions listed on Table III. Chromium, manganese and iron TPP (tetraphenylporphyrinato) nitrides were catalytically active whereas the corresponding halides were not. Cyclohexanol and cyclohexanone were the organic reaction products.

pressures of from about 15 to 1500 psig, preferably 30 to 750 psig. Again, depending upon whether the hydrocarbon is a solid, liquid, or gas, it is dissolved in or bubbled through a solvent such as benzene or acetic acid, or through the liquid hydrocarbon, neat, together with air or oxygen, for periods of time necessary to provide the desired product. The ratio of catalyst to substrate may vary, but is generally from about $10^{-6}$ to $10^{-1}$ moles of catalyst per mole of hydrocarbon.

TABLE III

CYCLOHEXANE OXIDATION[a]

| EXAMPLE | CATALYST | SOLVENT | MMOLES OF PRODUCT CYCLOHEXANOL | CYCLOHEXANONE | T.O.N. | T.O.N./hr. |
|---|---|---|---|---|---|---|
| 13 | Cr(TPP)Cl | neat | 0 | 0 | 0 | 0 |
| 14 | Cr(TPP)N | 50% benzene | 1.63 | 1.79 | 71 | 33 |
| 15 | Mn(TPP)Cl | neat | 0 | 0 | 0 | 0 |
| 16 | Mn(TPP)N | 50% benzene | 3.24 | 2.82 | 192 | 23 |
| 17 | Fe(TPP)Cl | neat | 0 | 0 | 0 | 0 |
| 18 | [Fe(TPP)]₂N | 50% benzene | 1.97 | 3.73 | 207 | 27 |
| 19 | Co (TPP)Cl | neat | 0 | 0 | 0 | 0 |

[a]Temp. = 100° C.; pressure is 500 psig of 10% $O_2$ in $N_2$; flowing at 5–10 cc/min; catalyst = 0.01–0.09 mmole/100 cc solvent.

From the foregoing results of Tables I–III it will readily be seen that when, for example, the acetylacetonate of a transition metal, as in Table I and II, or even the chloride of a metal complex, as in Table III, is substituted by a nitride of a metal complex, dramatic improvements in activity and yields are obtained.

In a further embodiment of this invention it has been found that non-ligated nitrides of certain transition metals are also surprisingly effective as catalysts in the oxidation of the aforedescribed hydrocarbons, and particularly alkanes and cycloalkanes, preferably those having from about 1 to 20 carbon atoms.

These catalysts may be defined as the transition metal nitrides of Groups IV(a) through VIII. Particularly effective among these are the nitrides of iron, manganese, chromium, and vanadium, and vanadium is the most preferred. The activity of these compounds as oxidation catalysts using air or oxygen under mild operating conditions in the liquid phase is quite surprising because they are virtually insoluble in the liquid medium, and thought to be quite stable.

The oxidation of hydrocarbons, most preferably alkanes, using these catalysts may be carried out in the same general way as the aforedescribed process employing the nitride metal complexes. That is to say, The products may range from alcohols and ketones to aldehydes and acids, but in the case of alkanes, they are generally alcohols and ketones, with little burn to CO and $CO_2$.

The following examples are illustrations of this particular embodiment of the invention.

Examples 20–52

In the following examples, a series of runs were carried out using the above-described transition metal nitrides on a variety of hydrocarbons under conditions described in Table IV, below. Products were analyzed by standardized gas chromatography.

These runs were carried out as follows: The catalyst and 30 ml hexane were added to a 30 ml Fisher-Porter aerosol tube equipped with a magnetic stirrer and gas inlet tubes. The reaction was carried out at 100°–200° C. under 100 psig of $O_2$. The major products were 1- and 2- hexanol, and 1- and 2- hexanone with some $C_2$–$C_6$ carboxylic acids also being formed.

In this table, activity of the catalyst is measured in terms of $O_2$ uptake. From these results it can be seen that nitrides are effective oxidation catalysts, and vanadium nitride is particularly effective.

TABLE IV

OXIDATION OF ALKANES AND CYCLOALXANES WITH METAL NITRIDES

| EXAMPLE | CATALYST | SUBSTRATE | SOLVENT | TEMP (C.°) | TIME (HRS) | $O_2$ UPTAKE (MMOLES) |
|---|---|---|---|---|---|---|
| 20 | Mn₃N | n-Hexane | — | 100 | 6 | 0 |
| 21 | Mn₃N | n-Hexane | — | 100 | 12 | 3.6 |

TABLE IV-continued
OXIDATION OF ALKANES AND CYCLOALXANES WITH METAL NITRIDES

| EXAMPLE | CATALYST | SUBSTRATE | SOLVENT | TEMP (C.°) | TIME (HRS) | $O_2$ UPTAKE (MMOLES) |
|---------|----------|-----------|---------|------------|------------|------------------------|
| 22 | CrN | n-Hexane | — | 100 | 6 | 0 |
| 23 | CrN | n-Hexane | — | 100 | 12 | 4.2 |
| 24 | $Fe_3N$ | n-Hexane | — | 100 | 6 | 0.6 |
| 25 | $Fe_3N$ | n-Hexane | — | 120 | 6 | 1.8 |
| 26 | VN | n-Hexane | — | 100 | 6 | 3.6 |
| 27 | VN | n-Hexane | — | 120 | 6 | 22.2 |
| 28 | VN | n-Hexane | — | 120 | 6 | 19.2 |
| 29 | VN | i-Butane | Benzene | 80 | 6 | 1.5 |
| 30 | VN | i-Butane | — | 100 | 6 | 6.3 |
| 31 | VN | Cyclohexane | — | 100 | 6 | 0.3 |
| 32 | $V_2O_3$ | n-Hexane | — | 100 | 6 | 0 |
| 33 | $V_2O_3$ | n-Hexane | — | 120 | 6 | 0 |
| 34 | $V_2O_4$ | n-Hexane | — | 100 | 6 | 1.5 |
| 35 | $V_2O_4$ | n-Hexane | — | 120 | 6 | 0 |
| 36 | $V_2O_5$ | n-Hexane | — | 100 | 6 | 0 |
| 37 | $V_2O_5$ | N—Hexane | — | 120 | 6 | 1.2 |
| 38 | $CpV(CO)_4$[a] | n-Hexane | — | 100 | 6 | 0 |
| 39 | $V(acac)_3$ | n-Hexane | — | 100 | 6 | 0 |
| 40 | $VO(acac)_2$ | n-Hexane | — | 100 | 6 | 20.4 |
| 41 | $VO(acac)_2$ | n-Hexane | — | 120 | 6 | 21.0 |
| 42 | VO(Oxalate) | n-Hexane | — | 100 | 6 | 1.8 |
| 43 | VO(Oxalate) | n-Hexane | — | 120 | 6 | 15.6 |
| 44 | VO(Pc) | n-Hexane | — | 100 | 6 | 0 |
| 45 | VN | n-Hexane | — | 120 | 3.5 | 2.4 |
| 46 | VN | n-Hexane | — | 120 | 9.5 | 14.0 |
| 47 | VN | n-Hexane | — | 120 | 3.5 | 1.8 |
| 48 | VN | n-Hexane | — | 120 | 9.5 | 3.6 |
| 49 | VN | n-Hexane | — | 120 | 3.5 | 4.8 |
| 50 | VN | n-Hexane | — | 120 | 9.5 | 9.7 |
| 51 | VN | n-Hexane | — | 120 | 3.5 | 3.0 |
| 52 | VN | n-Hexane | — | 120 | 9.5 | 14.1 |

[a]$CpV(CO)_4$ = cyclopentadienyl $V(CO)_4$.

What we claim is:

1. In a process in which an alkane is selectively oxidized by contact with air or oxygen in the presence of a catalyst comprising a Group IV(a) to VIII transition metal coordination complex, the improvement which comprises activiting said catalyst with nitride.

2. The process according to claim 1 wherein the alkane has from 1 to about 20 carbon atoms.

3. The process according to claim 1 wherein said alkane has from 1 to about 10 carbon atoms.

4. The process according to any of claims 1, 2 or 3 wherein the products of the oxidation are alcohols, ketones, or mixtures thereof.

5. The process according to any of claims 1, 2 or 3 wherein the products of the oxidation are alcohols, ketones, acids, esters, or mixtures thereof.

6. The process according to any of claims 1, 2 or 3 wherein the oxidation is carried out in the presence of an organic solvent.

7. The process according to any one of claims 1, 2 or 3 wherein the transition metal is selected from the group consisting of Ti, V, Cr, Mn, Fe, Co, Nb, Mo, Ru, Rh, W, Os and Ir.

8. The process according to any one of claims 1, 2 or 3 wherein the transition metal coordination complex contains a member selected from the group consisting of porphycenes, porphyrins, phthalocyanines, 1,3-bis-(arylimino)isoindolines, acetylacetonates, acetates, hydroxides, Schiff bases, propanates, butyrates, benzoates, naphthenates, stearates, bipyridines, terpyridines, phenanthrolines, dithiocarbamates, xanthates, cyclam, dioxocyclam and pyrazoylborates.

9. In a process in which an alkane is oxidized with air or oxygen in the presence of a Group IV(a) to VIII transition metal catalyst, the improvement which comprises employing as said catalyst a nitride of a transition metal of Group IV(a) to VIII.

10. The process according to claim 9 wherein the nitride is selected from the group consisting of manganese nitride, iron nitride, chromium nitride and vanadium nitride.

11. The process according to claim 9 wherein said alkane has from 1 to about 20 carbon atoms.

12. The process according to any of claims 9, 10 or 11 wherein the products of the oxidation are alcohols, ketones, or mixtures thereof.

13. The process according to any of claims 9, 10 or 11 wherein the products of the oxidation are alcohols, ketones, acids, esters, or mixtures thereof.

14. The process according to any of claims 9, 10 or 11 wherein the oxidation is carried out in the presence of an organic solvent.

15. The process according to claim 8 wherein the products of the oxidation are alcohols, ketones or mixtures thereof.

16. The process according to claim 8 wherein the products of the oxidation are alcohols, ketones, acids, esters, or mixtures thereof.

17. The process according to claim 8 wherein the oxidation is carried out in the presence of an organic solvent.

18. The process according to claim 9 wherein the products of the oxidation are alcohols, ketones or mixtures thereof.

19. The process according to claim 9 wherein the products of the oxidation are alcohols, ketones, acids, esters, or mixtures thereof.

20. The process according to claim 9 wherein the oxidation is carried out in the presence of an organic solvent.

* * * * *